United States Patent
Dane et al.

(10) Patent No.: US 9,186,430 B2
(45) Date of Patent: Nov. 17, 2015

(54) APPARATUS AND METHOD FOR ACCESSING A BIOLOGICAL INDICATOR WITHIN A CONTAINER

(75) Inventors: Gary T. Dane, Bow, NH (US); Tony Foley, Manchester, NH (US)

(73) Assignee: Symmetry Medical Manufacturing Inc., Warsaw, IN (US)

( * ) Notice: Subject to any disclaimer, the term of this patent is extended or adjusted under 35 U.S.C. 154(b) by 1037 days.

(21) Appl. No.: 13/296,382

(22) Filed: Nov. 15, 2011

(65) Prior Publication Data

US 2012/0156090 A1    Jun. 21, 2012

Related U.S. Application Data

(60) Provisional application No. 61/423,729, filed on Dec. 16, 2010.

(51) Int. Cl.
*A61L 2/28*    (2006.01)
*C12Q 1/22*    (2006.01)

(52) U.S. Cl.
CPC .... *A61L 2/28* (2013.01); *C12Q 1/22* (2013.01)

(58) Field of Classification Search
CPC .................................. A61L 2/28; C12Q 1/22
USPC ......... 422/430, 568, 119, 292, 295, 297–300; 435/29, 31–33, 287.4
See application file for complete search history.

(56) References Cited

U.S. PATENT DOCUMENTS

| | | | |
|---|---|---|---|
| 5,620,656 A | 4/1997 | Wensky et al. | |
| 6,193,931 B1* | 2/2001 | Lin et al. | 435/287.4 |
| 2002/0022246 A1 | 2/2002 | Lin et al. | |
| 2002/0058296 A1 | 5/2002 | Miller et al. | |
| 2003/0162243 A1* | 8/2003 | Foltz et al. | 435/31 |
| 2005/0014214 A1 | 1/2005 | Eveland et al. | |
| 2005/0229727 A1* | 10/2005 | Caderas | 73/866.5 |

* cited by examiner

*Primary Examiner* — Timothy Cleveland
(74) *Attorney, Agent, or Firm* — Hayes Soloway PC

(57) ABSTRACT

A biological indicator access apparatus and method thereof is provided. The apparatus includes a cage positioned at least partially within an interior compartment of a medical sterilization container, wherein the cage has an interior portion sized to house at least one biological indicator. At least one access element is removably coupled to the cage and permitting access to the interior portion, wherein the at least one access element is located exterior to the medical sterilization container. A filter material at least partially forms the interior portion of the cage, wherein the filter material allows a sterilization substance to traverse from within the interior compartment of the medical sterilization container to the interior portion and prevents non-sterile substances from traversing from the interior portion to the interior compartment of the medical sterilization container.

12 Claims, 4 Drawing Sheets

APPARATUS AND METHOD FOR ACCESSING A BIOLOGICAL INDICATOR WITHIN A CONTAINER

CROSS REFERENCE TO RELATED APPLICATION

This application claims benefit of U.S. Provisional Application Ser. No. 61/423,729 entitled, "Apparatus and method for accessing a biological indicator within a container," filed Dec. 16, 2010, the entire disclosure of which is incorporated herein by reference.

STATEMENT REGARDING FEDERALLY SPONSORED RESEARCH OR DEVELOPMENT

Not applicable.

FIELD OF THE DISCLOSURE

The present disclosure is generally related to biological indicators used with medical sterilization containers and more particularly is related to an apparatus and method for accessing a biological indicator within a container.

BACKGROUND OF THE DISCLOSURE

Articles such as medical instruments and the like are usually sterilized in a sterilization machine, such as an autoclave, in which the articles are exposed to high-pressure saturated steam for a relatively brief interval. Unless the articles are to be used immediately and in close proximity to the autoclave, it is desirable to sterilize the articles while they are inside a sterilization container. Once the sterilization process is complete, the medical instruments may be housed within the sterilization container until they are used for a medical procedure. To ensure a safe medical environment, medical staff must ensure that the medical instruments are fully sterilized and that the sterilization container hasn't become contaminated since the sterilization process. A medical practitioner may use a biological indicator within the sterilization container to indicate if the environment within the sterilization container is sterile or non-sterile. However, it is difficult if not impossible to access a biological indicator within a sterilization container without opening the sterilized container, and thus comprising the sterile integrity of the environment within the sterilization container.

Thus, a heretofore unaddressed need exists in the industry to address the aforementioned deficiencies and inadequacies.

SUMMARY OF THE DISCLOSURE

Embodiments of the present disclosure provide an apparatus and method for accessing a biological indicator within a medical sterilization container. Briefly described, in architecture, one embodiment of the apparatus, among others, can be implemented as follows. The biological indicator access apparatus includes a cage positioned at least partially within an interior compartment of a medical sterilization container, wherein the cage has an interior portion sized to house at least one biological indicator. At least one access element is removably coupled to the cage and permitting access to the interior portion, wherein the at least one access element is located exterior to the medical sterilization container. A filter material at least partially forms the interior portion of the cage, wherein the filter material allows a sterilization substance to traverse from within the interior compartment of the medical sterilization container to the interior portion and prevents non-sterile substances from traversing from the interior portion to the interior compartment of the medical sterilization container.

The present disclosure can also be viewed as providing methods of accessing a biological indicator within a medical sterilization container. In this regard, one embodiment of such a method, among others, can be broadly summarized by the following steps: positioning a cage at least partially within an interior compartment of the medical sterilization container, the cage having an interior portion at least partially formed by a filter material, wherein the filter material allows a sterilization substance to traverse from within the interior compartment of the medical sterilization container to the interior portion and prevents non-sterile substances from traversing from the interior portion to the interior compartment of the medical sterilization container; placing at least one biological indicator within the interior portion of the cage; subjecting the medical sterilization container to a sterilization process; and accessing the at least one biological indicator located within the interior portion of the cage through at least one access element located exterior to the medical sterilization container.

The present disclosure can also be viewed as a biological indicator system for use with a medical sterilization container. Briefly described, in architecture, one embodiment of the system, among others, can be implemented as follows. The biological indicator system includes a one-way filter cage removably positioned within an interior compartment of a medical sterilization container. At least one biological indicator is placed within the one-way filter cage. At least a first and a second access point to the one-way filter cage are provided, wherein both the first and second access points are removably sealed with at least one sealing element, wherein removal of the first access point permits removal of the one-way filter cage from the interior compartment of the sterilization container, and removal of the second access point does not permit removal of the one-way filter cage from the interior compartment of the sterilization container.

Other systems, methods, features, and advantages of the present disclosure will be or become apparent to one with skill in the art upon examination of the following drawings and detailed description. It is intended that all such additional systems, methods, features, and advantages be included within this description, be within the scope of the present disclosure, and be protected by the accompanying claims.

BRIEF DESCRIPTION OF THE DRAWINGS

Many aspects of the disclosure can be better understood with reference to the following drawings. The components in the drawings are not necessarily to scale, emphasis instead being placed upon clearly illustrating the principles of the present disclosure. Moreover, in the drawings, like reference numerals designate corresponding parts throughout the several views.

DETAILED DESCRIPTION

Figure 1:
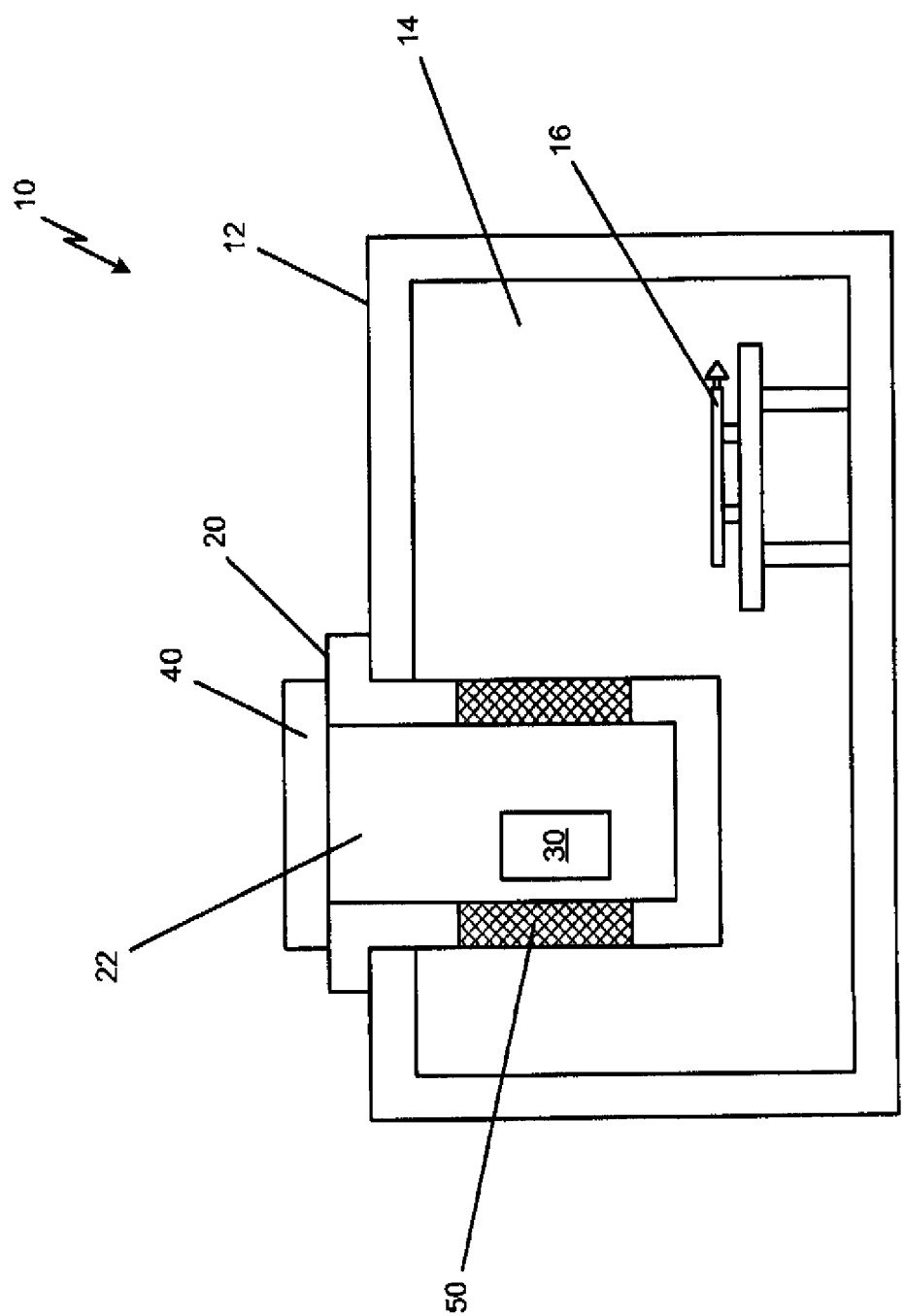
FIG. 1 is a cross-sectional illustration of a biological indicator access apparatus, in accordance with a first exemplary embodiment of the present disclosure.

FIG. 1 is a cross-sectional illustration of a biological indicator access apparatus 10, in accordance with a first exemplary embodiment of the present disclosure. The biological indicator access apparatus 10 includes a cage 20 positioned at least partially within an interior compartment 14 of a medical sterilization container 12. The cage 20 has an interior portion 22 sized to house at least one biological indicator 30. At least one access element 40 is coupled to the cage 20 and permits access to the interior portion 22. The at least one access element 40 is located exterior to the medical sterilization container 12. A filter material 50 at least partially forms the interior portion 22 of the cage 20. The filter material 50 allows a sterilization substance to traverse from within the interior compartment 14 of the medical sterilization container 12 to the interior portion 22 and prevents non-sterile substances from traversing from the interior portion 22 to the interior compartment 14 of the medical sterilization container 12.

The medical sterilization container 12 may include any sterilization container that has an interior compartment 14. This may include a sterilization container that is inserted into an external autoclave, or other sterilizing device, and/or a sterilization container that includes a sterilization substances and mediums within an interior compartment. The interior compartment 14 may be capable of holding a quantity of medical instruments 16 during a sterilization process and retaining the sterilized environment within the interior compartment 14 after the sterilization process is completed. As discussed further herein, the biological indicator 30 may be used to determine whether the interior compartment 14 is sterilized or non-sterile, thus indicating whether the medical instrument 16 is sterile or non-sterile.

Figure 2:
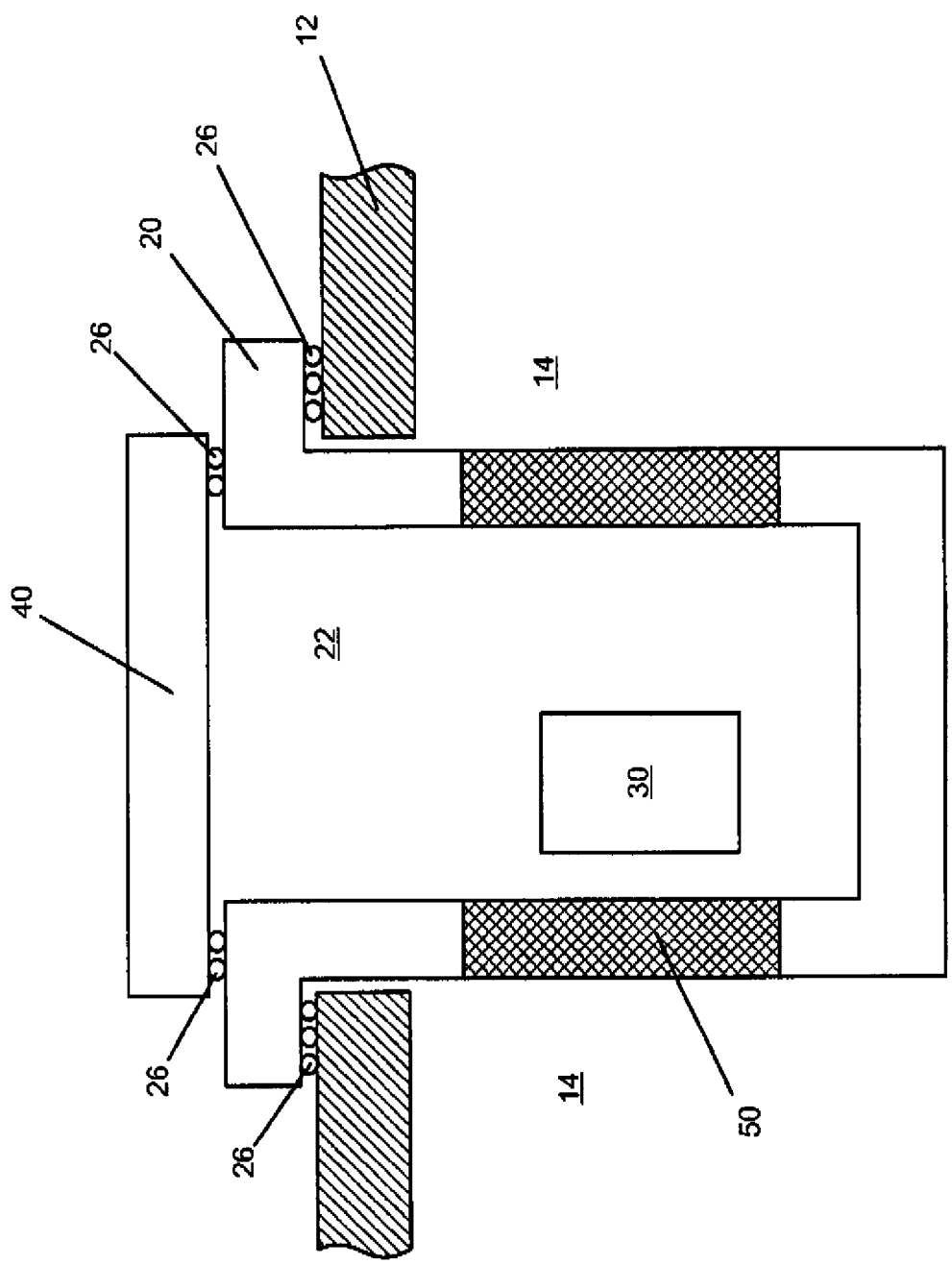
FIG. 2 is a cross-sectional illustration of the biological indicator access apparatus of FIG. 1, in accordance with the first exemplary embodiment of the present disclosure.

FIG. 2 is a cross-sectional illustration of the biological indicator access apparatus 10 of FIG. 1, in accordance with the first exemplary embodiment of the present disclosure. As is illustrated, the cage 20 is positioned at least partially within the interior compartment 14 of the medical sterilization container 12 and is sized to house at least one biological indicator 30 within an interior portion 22. The cage 20 may include a variety of structures, designs and configurations, all of which are considered within the scope of the present disclosure. In addition, the cage 20 may be constructed from any number of materials, including stainless steel, metal alloys, plastics and/or any combination thereof. The cage 20 may include any number or type of sealing element 26 located between the cage 20 and the medical sterilization container 12 and/or any other element. For example, the cage 20 may include a plurality of sealing elements 26, such as gaskets, in any and/or all joints and gaps formed proximate to the cage 20.

The cage 20 includes at least one access element 40 coupled to the cage 20. The access element 40 may include any type of structure, such as a door or dividing element, such that access to the interior portion 22 of the cage 20 is not permitted. The access element 40 may also provide a gastight, liquid-tight and/or sterilization material-tight within the interior portion 22 of the cage 20. Accordingly, when a sterilization process occurs, the access element 40 may not permit any release of a sterilization substance. The access element 40 is located exterior to the medical sterilization container 12. This configuration allows a user, such as a medical practitioner, to access the interior portion 22 of the cage 20 from outside of the medical sterilization container 12.

A filter material 50 at least partially forms the interior portion 22 of the cage 20. The filter material 50 may form any portion of the interior portion 22, which may include any configuration or amount of filter material 50 coupled to the cage 20. For example, the filter material 50 and cage 20 may be constructed as a one-way filter cage, where the filter material 50 is permanently bonded to the cage 20. For example, the filter material 50 may include a polytetrafluoroethylene (PTFE) material, commonly sold as GORE® Medical Membranes, or any other type of synthetic fluoropolymer of tetrafluoroethylene. The PTFE material may be capable of withstanding high temperatures that may be created within a sterilization environment and may have a high moisture vapor transmission rate (MVTR). A PTFE filter material 50 may include a polyester support material laminate constructed from any process, including heat stacked, ultrasonically welded and insert molded into the cage 20. A PTFE material may be capable of indefinite uses, thereby allowing the biological indicator access apparatus 10 to have a significant useful working life. Other materials that the filter material 50 may be formed from include high-density polyethylene fibers (HDPF), such as that sold under the trademark, TYVEK® by the DuPont™ company. However, HDPF may only be capable of enduring temperatures of approximately 260° F., and therefore, may only be used with steam sterilization processes under controlled conditions. Other filter materials 50 may include medical grade paper products, but these may be limited in their uses with steam sterilization processes.

The filter material 50 may allow a sterilization substance to traverse from within the interior compartment 14 of the medical sterilization container 12 to the interior portion 22. For example, during a sterilization process, the sterilization substance may properly sterilize a medical instrument 16 (FIG. 1) and may also traverse into the interior portion 22 of the cage 20 through the filter material 50. As the sterilization substance traverses into the interior portion 22, it may interact with the biological indicator 30. Accordingly, the biological indicator 30 may provide an indication of contact with the sterilization substance, which is indicative of a fully sterilized environment within the medical sterilization container 12.

Additionally, the filter material 50 may prevent any non-sterile substances from traversing from the interior portion 22 to the interior compartment 14 of the medical sterilization container 12. For example, after a sterilization process is performed, the medical sterilization container 12 may remain sealed to prevent contamination of any medical instruments 16 (FIG. 1) within the interior compartment 14. However, a medical practitioner may desire to determine whether the interior compartment 14 was properly sterilized, which can be done by checking the biological indicator 30. The medical practitioner may open the access element 40 to gain access to the interior portion 22 of the cage. When the access element 40 is opened, the atmosphere external to the medical sterilization container 12, having a plurality of non-sterile particles, may flow into the interior portion 22, thus contaminating the interior portion 22. However, the filter material 50 may prevent the atmosphere and any non-sterile particles and/or substances from traversing into the interior compartment 14 of the medical sterilization container 12. Accordingly, this allows the biological indicator 30 to be accessed without compromising the integrity of the sterilized environment within the interior compartment 14, thereby ensuring that the medical instruments 16 (FIG. 1) can be used in a medical procedure.

The biological indicator 30 used with the biological indicator access apparatus 10 may include a variety of devices that are capable of indicating a biological content within the interior compartment 14 of the medical sterilization container 12. This may include an indicator strip, such as the 3M® Attest® Biological indicator, or any other type of indicator strip positioned fully within the interior portion 22 of the cage 20. The biological indicator 30 may also include an indicator label, such as a temperature indicating label like the Tempilable® label sold by the Tempil Corporation, which may be positioned fully within the interior portion 22 of the cage 20. The temperature indicator label may indicate when a specific temperature is reached within the interior portion 22 of the cage 20 from a sterilization process. The specific temperature may be one, which eliminates all biological content from within the interior compartment 14 of the medical sterilization container 12. Accordingly, when the sterilization process is completed, the temperature indicator strip may indicate that the temperature has been reached and the interior compartment is sterile.

The biological indicator 30 may also include an electronic sterility indicator, or another type of electronic biological content indicator, located within the interior portion 22 of the cage 20. The biological indicator 30 may monitor the biological content within the interior compartment 14 and record a quantity data corresponding to a number of conditions and characteristics within the interior compartment 14. For example, the biological indicator 30 may record a monitored biological content, an aspect of the sterilization process such as the date, time and/or temperature. The biological indicator 30 may also record a log history of the sterilization of the medical sterilization container 12.

Figure 3:
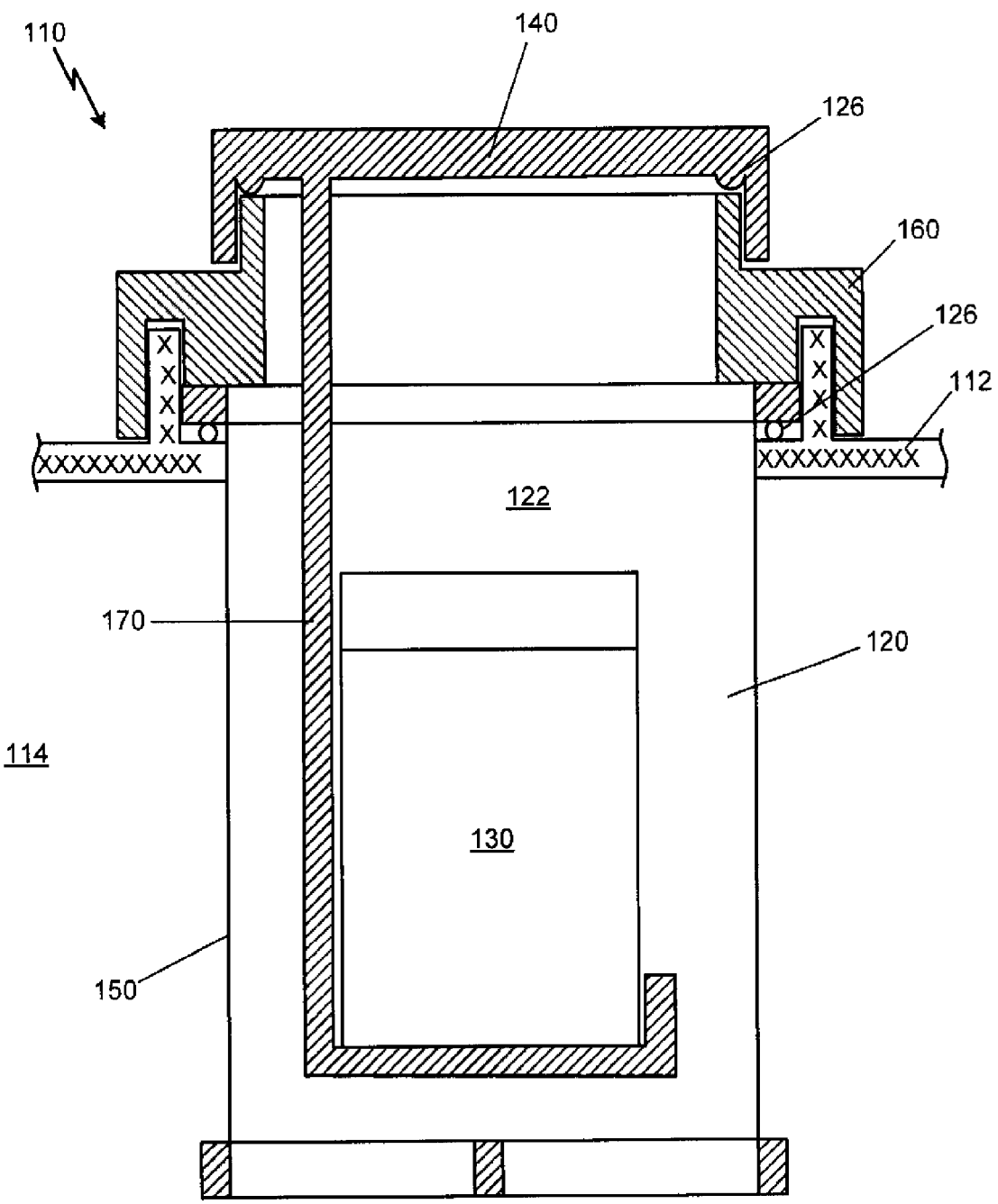
FIG. 3 is a cross-sectional illustration of a biological indicator access apparatus, in accordance with a second exemplary embodiment of the present disclosure.

FIG. 3 is a cross-sectional illustration of a biological indicator access apparatus, in accordance with a second exemplary embodiment of the present disclosure. The biological indicator access apparatus 110 includes a cage 120 positioned at least partially within an interior compartment 114 of a medical sterilization container 112. The cage 120 has an interior portion 122 sized to house at least one biological indicator 130. At least one access element 140 is coupled to the cage 120 and permits access to the interior portion 122. The at least one access element 140 is located exterior to the medical sterilization container 112. A filter material 150 at least partially forms the interior portion 122 of the cage 120. The filter material 150 allows a sterilization substance to traverse from within the interior compartment 114 of the medical sterilization container 112 to the interior portion 122 and prevents non-sterile sterilize from traversing from the interior portion 122 to the interior compartment 114 of the medical sterilization container 112.

The biological indicator access apparatus 110 also includes a secondary access element 160 positioned between the access element 140 and the cage 120. The secondary access element 160 may be used to secure the cage to the medical sterilization container 112, as well as allow for removal and replacement of the cage 120 from the medical sterilization container 112. The secondary access element 160 may engage with part of the medical sterilization container 112, such as a structured tab or raised feature on the surface of the medical sterilization container 112, however any type of engagement, such as fasteners or threaded structures is considered within the scope of the present disclosure. The cage 120 may fit with the secondary access element 160 and be suspended within the interior compartment 114 of the medical sterilization container 112 using a rim structure of the cage 120. As is shown, the rim structure of the cage 120 may be sized larger than the aperture or hole within the medical sterilization container 112.

A number of sealing devices 126 may be used between the secondary access element 160 and the medical sterilization container 112, to prevent contamination of the cage 120 or the interior compartment 114 of the medical sterilization container 112. The sealing devices 126 may include rubberized or silicone based materials which create a contact seal between the cage 120 and the medical sterilization container 112 or the secondary access element 160, depending on design. When the secondary access element 160 is removed, the cage 120 may be removed from the medical sterilization container 112 fully, which allows for convenient repair or replacement of the cage 120.

The secondary access element 160 may also permit engagement with the at least one access element 140, such as by using threaded features to connect or disconnect the two structures. For example, the at least one access element 140 may engage with the secondary access element 160 through a ¼ turn fitting structure positioned between the two structures. As is shown in FIG. 3, removal of the at least one access element 140 from the secondary access element 160 may not permit the cage 120 to be removed from the medical sterilization container 112. Accordingly, when the at least one access element 140 is removed, a user may gain access to the interior portion 122 of the cage 120 without contaminating the interior compartment 114 of the medical sterilization container 112. This allows the biological indicator 130 within the cage 120 to be replaced, removed, or examined without contaminating any medical instruments located within the interior compartment 114.

Affixed to the at least one access element 140 is a hanging device 170 which may be used to support or hold a biological indicator 130, or any other container, such as a vial that houses a biological indicator 130. The hanging device 170 may include variations in design. For example, the hanging device 170 may include a suspended clamp or other device which clamps on or grasps the biological indicator 130, and holds it within the interior portion 122 of the cage 120 successfully. This may include holding the biological indicator 130 within the cage 120 without touching or making contact with the cage 120. As is shown in FIG. 3, the hanging device 170 may be a vial holding structure having an approximately horizontal surface for holding a vial. The suspended clamp may be sized to hold any type of container or structure as well, including vials or other containers that may be used to hold biological indicators. Any suspended clamp or other hanging device 170 used may have any number of platforms, textures, retention devices, or other structures to successfully hold the biological indicator 130 or other structure. In use, when the at least one access element 140 is removed from the secondary access element 160, the hanging device 170 and any structures supported thereby may be removed as well.

Figure 4:
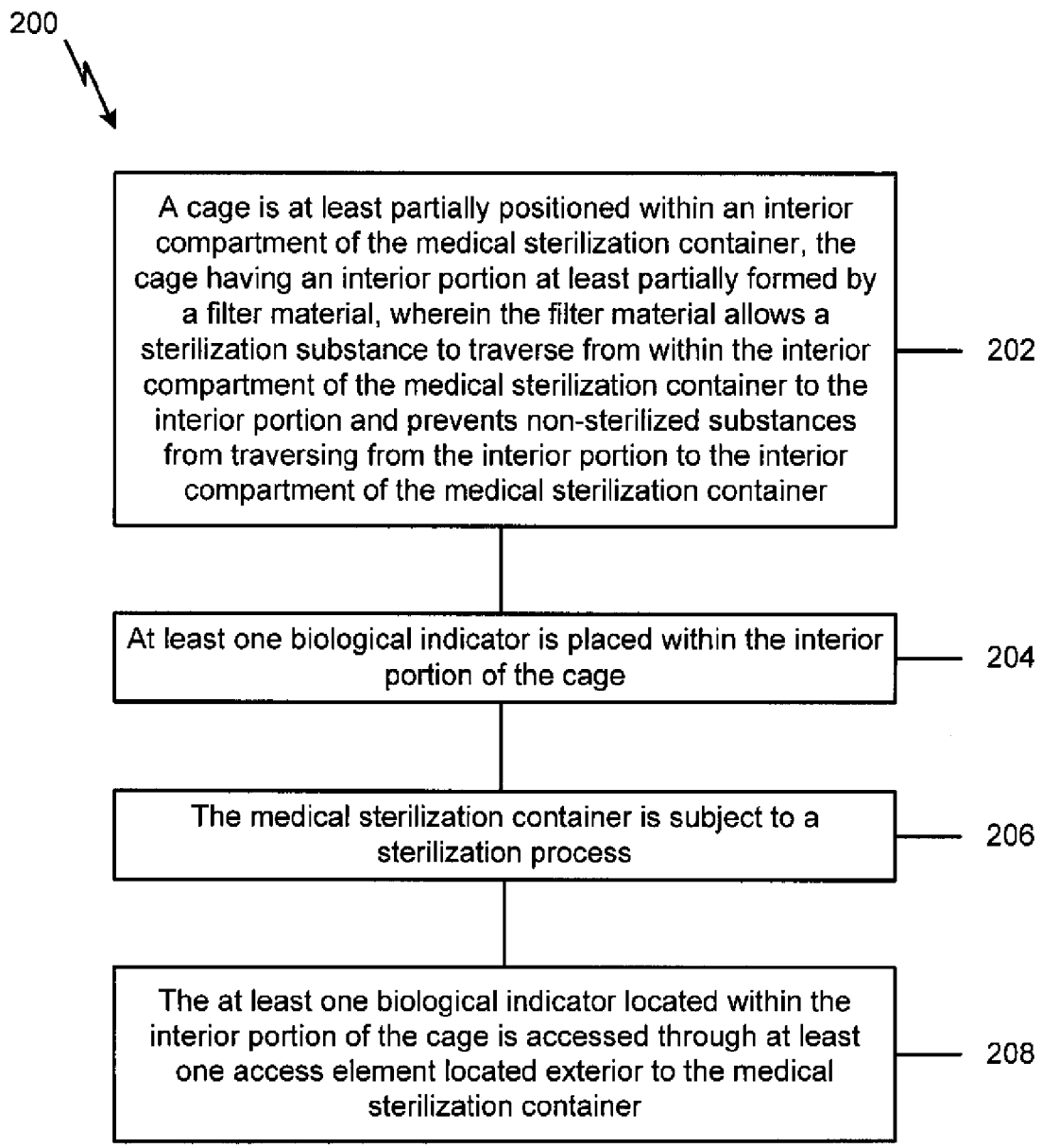
FIG. 4 is a flowchart illustrating method of accessing a biological indicator within a medical sterilization container, in accordance with the first exemplary embodiment of the present disclosure.

FIG. 4 is a flowchart 200 illustrating method of accessing a biological indicator within a medical sterilization container, in accordance with the first exemplary embodiment of the present disclosure. It should be noted that any process descriptions or blocks in flow charts should be understood as representing modules, segments, portions of code, or steps that include one or more instructions for implementing specific logical functions in the process, and alternate implementations are included within the scope of the present disclosure in which functions may be executed out of order from that shown or discussed, including substantially concurrently or in reverse order, depending on the functionality involved, as would be understood by those reasonably skilled in the art of the present disclosure.

As is shown by block 202, a cage is at least partially positioned within an interior compartment of the medical sterilization container, the cage having an interior portion at least partially formed by a filter material, wherein the filter material allows a sterilization substance to traverse from within the interior compartment of the medical sterilization container to the interior portion and prevents non-sterile substances from traversing from the interior portion to the interior compartment of the medical sterilization container (block 202). At least one biological indicator is placed within the interior portion of the cage (block 204). The medical sterilization container is subject to a sterilization process (block 206). The at least one biological indicator located within the interior portion of the cage is accessed through at least one access element located exterior to the medical sterilization container (block 208).

The method may include any additional number of steps and processes, as well as any of the features, structures, and/or steps disclosed with respect to FIGS. 1-3. For example, the cage may be sealed to the medical sterilization container, and the at least one access element may be sealed to the cage with a sealing element. The step of accessing the at least one biological indicator located within the interior portion of the cage through the at least one access element located exterior to the medical sterilization container further include unsealing a sealing element positioned between at least one of the cage to the medical sterilization container and the at least one access element to the cage. The cage or a biological indicator within the cage may be suspended within the interior compartment of the medical sterilization container with at least one hanging device. A biological indicator located within the interior portion of the cage may be accessed through the at least one access element located exterior to the medical sterilization container by removing the at least one access element without compromising a sterilized environment within the interior compartment of the medical sterilization container.

It should be emphasized that the above-described embodiments of the present disclosure, particularly, any "preferred" embodiments, are merely possible examples of implementations, merely set forth for a clear understanding of the principles of the disclosure. Many variations and modifications may be made to the above-described embodiment(s) of the disclosure without departing substantially from the spirit and principles of the disclosure. All such modifications and variations are intended to be included herein within the scope of this disclosure and the present disclosure and protected by the following claims.

What is claimed is:

1. A biological indicator access apparatus comprising:
   a cage positioned at least partially within an interior compartment of a medical sterilization container, wherein the cage has an interior portion sized to house at least one biological indicator;
   at least one access element removably coupled to the cage and permitting access to the interior portion, wherein the at least one access element is located exterior to the medical sterilization container;
   a filter material at least partially forming the interior portion of the cage, wherein the filter material allows a sterilization substance to traverse from within the interior compartment of the medical sterilization container to the interior portion and prevents non-sterile substances from traversing from the interior portion to the interior compartment of the medical sterilization container;
   at least one gasket positioned at least partially between the at least one access element and the cage; and
   at least one biological indicator positioned within the cage, wherein the at least one biological indicator is suspended within the cage with at least one hanging device.

2. The biological indicator access apparatus of claim 1, further comprising a sealing element positioned at least partially between the cage and the medical sterilization container.

3. The biological indicator access apparatus of claim 1, wherein the at least one gasket further comprises at least two gaskets, wherein a first of the at least two gaskets is positioned between the at least one access element and the cage, and a second of the at least two gaskets is positioned between that the cage and the medical sterilization container.

4. The biological indicator access apparatus of claim 1, wherein the cage is removable from the interior compartment of a medical sterilization container.

5. The biological indicator access apparatus of claim 1, wherein the filter material further comprises at least one of: a polytetrafluoroethylene material, a high-density polyethylene fiber material, and a medical grade paper material.

6. The biological indicator access apparatus of claim 1, wherein the at least one hanging device further comprises a rim structure of the cage positioned exterior of the medical sterilization container.

7. The biological indicator access apparatus of claim 1, wherein the at least one hanging device further comprises a suspended clamp, wherein the suspended clamp removably holds the biological indicator within the interior portion of the cage without making contact with the cage.

8. A biological indicator access apparatus comprising:
   a cage positioned at least partially within an interior compartment of a medical sterilization container, wherein the cage has an interior portion sized to house at least one biological indicator;
   at least one access element removably coupled to the cage and permitting access to the interior portion, wherein the at least one access element is located exterior to the medical sterilization container;
   a filter material at least partially forming the interior portion of the cage, wherein the filter material allows a sterilization substance to traverse from within the interior compartment of the medical sterilization container to the interior portion and prevents non-sterile substances from traversing from the interior portion to the interior compartment of the medical sterilization container; and
   at least one gasket positioned at least partially between the at least one access element and the cage; and
   a vial removably positioned within the cage and suspended within the cage with a vial holding structure, wherein the vial holding structure is connected to the at least one access element with at least one hanging device.

9. The biological indicator access apparatus of claim 1, wherein the at least one hanging device is suspended from the at least one access element.

10. The biological indicator access apparatus of claim 1, wherein the at least one biological indicator is positioned on a platform of the at least one hanging device.

11. The biological indicator access apparatus of claim 10, wherein the at least one biological indicator is positioned on the platform of the at least one hanging device without making contact with a base and a sidewall of the cage.

12. The biological indicator access apparatus of claim 1, wherein the filter material is positioned only on a sidewall of the cage.

* * * * *